US00PP13513P2

(12) United States Plant Patent
Carruth

(10) Patent No.: US PP13,513 P2
(45) Date of Patent: Jan. 28, 2003

(54) FLORIBUNDA ROSE PLANT NAMED 'WEKSANPOLY'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/995,029

(22) Filed: Nov. 27, 2001

(51) Int. Cl.[7] ..... A01H 5/00
(52) U.S. Cl. ..... Plt./150
(58) Field of Search ..... Plt./150, 151

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Floribunda rose suitable for garden decoration, having flowers of even medium red coloration.

1 Drawing Sheet

BOTANICAL CLASSIFICATION

*Rosa hybrida.*

VARIETY DENOMINATION

WEKsanpoly.

BACKGROUND OF THE INVENTION

This invention relates to a new and distinct variety of Floribunda Rose. The varietal denomination of the new variety is 'WEKsanpoly'. It has as its seed parent the variety known as 'POUlclaus' (U.S. Plant Pat. No. 9,063) and as its pollen parent an undisseminated seedling of my creation.

SUMMARY OF THE INVENTION

Among the features which distinguish the new variety from other presently available and commercial rose cultivars known to the inventor are the following combination of characteristics: its even lasting red coloration, its sepal inner surfaces that blush red with age, its rounded bushy growing habit and its deep red style coloration. The new variety has a rounded bushy to somewhat upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKsanpoly' may be asexually propagated by cuttings, budding and grafting.

COMPARISON WITH PARENTS

The new variety may be distinguished from its seed parent, 'Poulclaus' by the following combination of characteristics: whereas 'POUlclaus' bears small sized flowers (about 5 to 6.5 cm. in diameter) and foliage, 'WEKsanpoly' bears significantly larger flowers (6.9 to about 9.0 cm. in diameter) and foliage. The seed parent is classified as a miniature rose with a small mature growing habit, whereas 'WEKsanpoly' is classified as a floribunda rose with a significantly larger mature growing habit.

The new variety may be distinguished from its pollen parent, an undisseminated seedling of my creation, by the following combination of characteristics: whereas the undisseminated seedling bears semi-double flowers (about 7 to about 12 petals) and medium-large foliage, 'WEKsanpoly' bears double flowers with significantly higher petalage (about 18 to about 26 petals) and significantly smaller foliage. The new variety has a rounded bushy to somewhat upright growing habit with dark red new shoots whereas the pollen parent has a significantly more spreading growing habit with green new shoots.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Kern County, Calif. in the month of September. Phenotypic expression may vary with environmental, cultural and climatic conditions, as well as differences in conditions of light and soil.

FLOWER

The new variety sometimes bears its flowers singly, sometimes in clusters of three to four or more per stem. Flowers may be borne in regular flat to somewhat rounded clusters on strong medium stems (about 52 to about 80 cm.). Outdoors, the plant blooms abundantly and nearly continuously during the growing season. The flowers have a slight tea fragrance.

BUD

The peduncle is about 4.1 to about 5.8 cm. in length, of average to somewhat heavy caliper (about 0.2 to about 0.4 cm. in diameter), and usually erect to somewhat stiff. It is somewhat smooth, with some coarse stipitate glands and very few hairs. Peduncle color is between 144B and 148D often moderatly suffused, especially on the side exposed to the sun, with between 183B and 187C.

Before the calyx breaks, the bud is about 1.0 to about 1.5 cm. in diameter at the widest point, about 1.4 to about 2.3 cm. in length, and very pointed in shape. The surface of the bud bears few foliaceous appendages and some stipitate glands, usually with slender slightly cut foliaceous parts extending beyond the tip of the bud about ¼ or more of its length. Bud color is between 144A and 148C sometimes lightly suffused, especially on the side exposed to the sun, with between 183A and 187C.

Before the calyx breaks, the bud is about 1.0 to about 1.5 cm. in diameter at the widest point, about 1.4 to about 2.3 cm. in length, and very pointed in shape. The surface of the bud bears few foliaceous appendages and some stipitate glands, usually with slender slightly cut foliaceous parts extending beyond the tip of the bud about ¼ or more of its length. Bud color is between 144A and 148C sometimes lightly suffused, especially on the side exposed to the sun, with between 183A and 187C.

The sepals are about 1.8 to about 3.1 cm. in length and about 0.7 to about 1.1 cm. in width at the widest point. The outer surface color of the sepal is between 144A and 148C sometimes lightly suffused, especially on the side exposed to the sun, with between 183A and 187C. The inner surface of the sepal is covered with fine wooly tomentum; sepal margins are lined with many stipitate glands and hairs. Color of the inner surface of the sepal is between 139C and 148D. As the sepals begin to open, when the calyx breaks, sometimes a blush color between 183D and 185C develops on the inner surface of the sepals. As the flower matures, the inner surface of the sepal often blushes over the entire surface with a suffusion of between 183C and 185B.

As the petals open (after the calyx breaks), the bud is about 1.2 to about 2.2 cm. in diameter at the widest point, about 1.8 to about 2.6 cm. in length, and very pointed to somewhat ovoid in form. The color of the under surfaces of the newly opened petals is between 53A and 60A. At the point where the petal attaches, there is a small zone of near 3C. The color of the upper surfaces of the newly opened petals is between 53A and 60A. At the point where the petal attaches, there is a moderately small zone of between 6B and 7C.

BLOOM

When fully open, the bloom ranges from about 6.5 to about 9.0 cm. in diameter. Petalage is double with about 18 to 26 petals and about 1 to 3 petaloids irregularly arranged. When partially open, the bloom form is moderately cupped to somewhat high centered, and the petals are moderately cupped to somewhat spiraled and slightly undulated with petal edges sometimes very reflexed inward but usually moderately reflexed outward. When fully open, the bloom form is more cupped to flat, and the petals are loosely cupped to more undulated with petal edges moderately reflexed outward.

PETALS

The substance of the petals is somewhat heavy and of medium thickness, with upper surfaces moderately satiny to slightly velvety and under surfaces slightly shiny to matte. The outer petals are broadly obovate in shape with rounded apices. The inner petals are moderately oblanceolate to somewhat obovate in shape with rounded to sometimes emarginated apices. The petals are about 2.6 to about 4.2 cm. in length and 2.1 to about 3.3 cm. in width at the widest point. Petal margins are mostly entire to sometimes slightly irregularly crenate.

NEWLY OPENED FLOWER

The under surface color of the outer, intermediate and inner petals is between 53C and 60A. At the point where the petal attaches, there is a small zone of near 5C. The upper surface color of the outer, intermediate and inner petals is between 45A and 53B. At the point where the petal attaches, there is a moderately small zone of near 9C.

The general tonality of the newly opened flower is between 45A and 53B.

THREE-DAY-OLD FLOWER

The under surface color of the outer and inner petals is between 53D and 60A. At the point where the petal attaches, there is a small zone of between 3D and 2D. The upper surface color of the outer and inner petals is between 46A and 53B. At the point where the petal attaches, there is a moderately small zone of between 5C and 6C.

The general tonality of the three-day-old flower is between 46A and 53B.

On the spent bloom, the petals usually drop off cleanly.

In September in Kern County, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 103) and are arranged regularly about the pistils; a few are mixed with petaloids. The filaments are variable in length (about 0.3 to about 0.6 cm.), most with anthers. Filaments are near 6C at the base and between 12A and 13B near the top often suffused with near 33B. The anthers are of medium size and all open approximately at the same time. Anther color is between 16A and 20A when immature and between 200C and 164B at maturity. Pollen is very abundant.

FEMALE REPRODUCTIVE ORGANS

Pistils vary in number (average about 83). The styles are moderately uneven to somewhat long in length (about 0.6 to about 0.9 cm.), somewhat heavy in caliper, and very loosely bunched. Stigma color is between 13D and 18C. Style color is between 2C and 1C often heavily suffused near the top with near 53A. Ovaries are usually all enclosed in the calyx.

Hips are of average length (about 1.7 to about 2.4 cm.), moderately globular in form, and between 28A and 33B in color when ripe. The hip surface is very smooth with thick fleshy walls. The sepals are moderately permanent, somewhat long in length, and usually straight in shape. The seeds are irregularly rounded, smooth in texture, approximately 10 to about 15 per hip, about 0.3 to about 0.6 cm. in diameter at the widest point and between 160C and 162C in color.

FOLIAGE

The compound leaves are usually comprised of three to five or more leaflets and are borne abundantly. The five-leaflet leaves are about 6.1 to about 10.5 cm. in length and about 5.1 to about 8.2 cm. in width at the widest point, somewhat heavy to leathery in texture, and moderately glossy in finish. The terminal leaflets are about 2.8 to about 5.6 cm. in length and about 1.6 to about 3.3 cm. in width at the widest point, shaped broadly oval to somewhat ovate with moderately acute apices and moderately rounded to somewhat acute bases. Their margins are usually simply serrate.

The upper surface color of the mature leaf is between 147A and 139A. The under surface color of the mature leaf is between 147B and 139C. The upper surface color of the young leaf is between 147A and 138B, sometimes lightly suffused with between 187A and 187B. The under surface color of the young leaf is between 147B and 138C, sometimes lightly suffused with between 187B and 187C.

The rachis is somewhat light in caliper and almost smooth. The upper side is shallowly grooved with few hairs and some stipitate glands on the edges of the grooves. The under side of the rachis is almost smooth with few stipitate glands and very few small prickles. The rachis color is between 144B and 145A.

The stipules are about 0.7 to about 1.2 cm. in length and of medium width (about 0.5 to about 0.7 cm.) with medium to somewhat long straight points that usually turn out at an angle of more than 45 degrees, sometimes recurving toward the stem. The stipule color is between 137C and 147B.

The petiole is about 0.7 to about 1.4 cm. in length and about 0.1 to about 0.2 cm in diameter at the widest point. The petiole color is between 137C and 147B.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a rounded bushy to somewhat upright low to medium height growing habit (about 88 to about 105 cm. in height and about 72 to about 88 cm. spread at the widest point), with full branching. It displays moderately vigorous growth and the canes are of somewhat small to medium caliper for the class.

The color of the major stems is near 146B. They bear some large prickles that are about 0.6 to about 1.1 cm. in length. The large prickles are almost straight to angled slightly downward with a medium length somewhat broad oval base; prickle color is between 164A and 165B. The major stem bears few medium sized and few small prickles of similar shape and coloration.

The color of the branches is between 144A and 148C. They bear few large prickles which are of similar size and shape to the large prickles on the major stems; prickle color is between 160B and 160C. The branches bear some medim sized and some small prickles of similar shape and coloration and few stipitate glands.

The color of the new shoots is between 144A and 148C. They bear few large prickles which are of similar size and shape to the large prickles on the major stems; prickle color is between 1C and 160B sometimes lightly suffused with between 183D and 185C. The shoots bear some medium sized and some small prickles of similar shape and coloration and few stipitate glands.

I claim:

1. A new and distinct Floribunda rose plant of the variety substantially as described and illustrated herein.

* * * * *

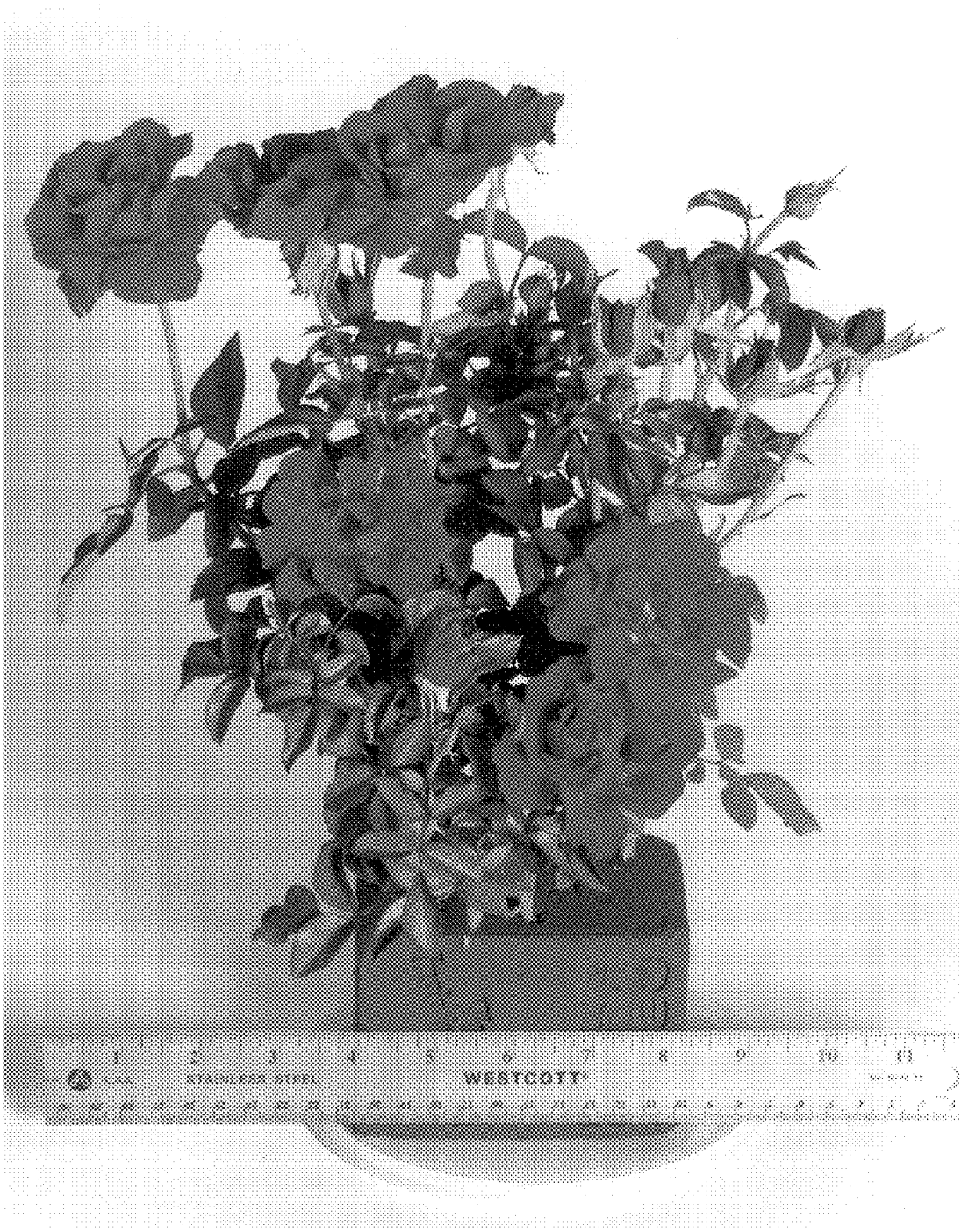
WESTCOTT